US 011230758B2

(12) United States Patent
Pretorius et al.

(10) Patent No.: US 11,230,758 B2
(45) Date of Patent: Jan. 25, 2022

(54) TIP FOR AN ULTRASONIC SURGICAL TOOL WITH CASE HARDENED CUTTING EDGES AND METHOD OF MAKING SAME

(71) Applicant: Stryker European Holdings I, LLC, Kalamazoo, MI (US)

(72) Inventors: Neels Pretorius, Glanmire (IE); Kevin Manley, Cobh (IE); Gerard Nunan, Ballincolig (IE); Lorena Monzon, Cloyn (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 292 days.

(21) Appl. No.: 16/326,524

(22) PCT Filed: Sep. 15, 2017

(86) PCT No.: PCT/US2017/051709
§ 371 (c)(1),
(2) Date: Feb. 19, 2019

(87) PCT Pub. No.: WO2018/053223
PCT Pub. Date: Mar. 22, 2018

(65) Prior Publication Data
US 2019/0223899 A1 Jul. 25, 2019

Related U.S. Application Data

(60) Provisional application No. 62/395,764, filed on Sep. 16, 2016.

(51) Int. Cl.
*C23C 8/04* (2006.01)
*B23K 26/142* (2014.01)
(Continued)

(52) U.S. Cl.
CPC .............. *C23C 8/04* (2013.01); *B23K 26/142* (2015.10); *B23K 26/354* (2015.10); *A61B 2017/00526* (2013.01)

(58) Field of Classification Search
CPC ...... C23C 8/04; B23K 26/142; B23K 26/354; A61B 2017/00526; A61B 17/320068;
(Continued)

(56) References Cited

U.S. PATENT DOCUMENTS 5,391,144 A * 2/1995 Sakurai ............ A61B 17/22012
604/22
5,836,765 A 11/1998 Hickok
(Continued)

FOREIGN PATENT DOCUMENTS

JP H0595955 A 4/1993
JP H06114069 A 4/1994
(Continued)

OTHER PUBLICATIONS

International Search Report and Written Opinion for PCT/US2017/051709 dated Sep. 15, 2017; 13 pages.
(Continued)

*Primary Examiner* — Sarang Afzali
(74) *Attorney, Agent, or Firm* — Howard & Howard Attorneys PLLC

(57) ABSTRACT

A tip is formed for use with an ultrasonic handpiece. The handpiece, when actuated, is capable of causing the tip to go into ultrasonic vibrations. The tip has a shaft from which a head extends. Teeth extend from the head. At least the teeth have a case hardened outer layer. The case hardened outer layer reduces the wearing of the teeth when the teeth are vibrated against hard tissue.

23 Claims, 7 Drawing Sheets

(51) Int. Cl.
*B23K 26/354* (2014.01)
*A61B 17/00* (2006.01)

(58) Field of Classification Search
CPC ............ A61B 17/1659; A61B 17/1671; A61B 2017/00261; A61B 2017/320004; A61B 2017/320072; A61B 2017/320078
See application file for complete search history.

(56) References Cited

U.S. PATENT DOCUMENTS

| | | | |
|---|---|---|---|
| 6,077,282 | A | 6/2000 | Shturman et al. |
| 6,129,735 | A | 10/2000 | Okada et al. |
| 6,698,415 | B2 | 3/2004 | Garcia et al. |
| 9,340,848 | B2 | 5/2016 | Pinzl |
| 10,010,339 | B2 * | 7/2018 | Witt .................. A61L 31/14 |
| 10,046,362 | B2 | 8/2018 | Akagane |
| 10,449,570 | B2 * | 10/2019 | Downey ............... B06B 1/0253 |
| 10,864,011 | B2 * | 12/2020 | Downey ............... A61B 17/142 |
| 10,888,347 | B2 * | 1/2021 | Witt ............ A61B 17/320092 |
| 10,893,883 | B2 * | 1/2021 | Dannaher ................ A61N 7/00 |
| 2005/0177184 | A1 | 8/2005 | Easley |
| 2007/0293875 | A1 | 12/2007 | Soetikno et al. |
| 2009/0143806 | A1 | 6/2009 | Witt et al. |
| 2010/0057118 | A1 | 3/2010 | Dietz et al. |
| 2012/0239068 | A1 * | 9/2012 | Morris ........... A61B 17/320068 606/169 |
| 2013/0123819 | A1 | 5/2013 | Genau et al. |
| 2015/0005795 | A1 | 1/2015 | Darian et al. |
| 2015/0191814 | A1 | 7/2015 | Stout et al. |
| 2016/0082534 | A1 | 3/2016 | Fujiwara et al. |

FOREIGN PATENT DOCUMENTS

| | | |
|---|---|---|
| JP | 2014506287 A | 3/2014 |
| WO | 2012079025 A1 | 6/2012 |
| WO | 2015072326 A1 | 5/2015 |

OTHER PUBLICATIONS

English language abstract and machine-assisted English translation for JPH 05-95955 A extracted from espacenet.com database on Aug. 9, 2021, 5 pages.

English language abstract and machine-assisted English translation for JPH 06-114069 A extracted from espacenet.com database on Aug. 9, 2021, 8 pages.

English language abstract for JP 2014-506287 A extracted from espacenet.com database on Aug. 9, 2021, 2 pages.

English language abstract for WO 2015/072326 A1 extracted from espacenet.com database on Aug. 9, 2021, 2 pages.

* cited by examiner

TIP FOR AN ULTRASONIC SURGICAL TOOL WITH CASE HARDENED CUTTING EDGES AND METHOD OF MAKING SAME

CROSS-REFERENCE TO RELATED APPLICATIONS

This patent application claims priority to and all advantages of International Patent Application No. PCT/US2017/051709 filed Sep. 15, 2017, which claims priority to and all advantages of U.S. Provisional Patent Application No. 62/395,764 filed Sep. 16, 2016, the entire contents of both of which are incorporated herein by reference.

FIELD OF THE INVENTION

This description relates generally to a tip of an ultrasonic surgical tool. More particularly, this description relates to a tip with hardened teeth that resist wear and a method of making the tip.

BACKGROUND

The availability of powered surgical tools has both improved the ability to perform surgical procedures and has made it possible to perform some procedures that, previously, were difficult, if not impossible, to perform.

One such powered surgical tool is the ultrasonic handpiece. This type of tool includes three basic components. There is the handpiece itself. Internal to the handpiece are one or more drivers. The drivers, upon the application of AC drive signal, cyclically expand and contract at a relatively high frequency, typically at least 10 kHz or more. A console, the second component, provides the AC drive signal. The tip is the third component of the tool. The tip is mechanically coupled to and extends forward from the drivers. At the distal end, the tip has a head. The head is formed with teeth. The vibrations of the drivers cause like vibrations of the head and, by extension, the teeth. When the vibrating teeth are applied to hard tissue such as bone, the back and forth movement of the teeth shear away, remove, the tissue. When an ultrasonic tool is actuated the teeth typically engage in a relatively narrow range of motion, often 5 mm or less. This makes the ultrasonic surgical tool a very useful tool for precisely removing small masses of hard tissue. Thus, ultrasonic tools have proven to be very practical tools for, at any given instant, removing a small section of bone in procedures such as laminectomies.

Owing to the delicate nature of the surgical procedures that ultrasonic tools are used to perform, it should be appreciated that the tips of these tools are relatively small in size. It is not uncommon for the head of the tip to have a length of 20 mm or less and a diameter of 5 mm or less. A head may have three or more teeth. Each tooth may have a base to peak height of 3 mm or less and a cross width of 5 mm or less.

Generally, ultrasonic tools work reasonably well for the purposes for which these tools are designed. Sometimes though, the application of the teeth to hard tissue can result in appreciable wear of the teeth. This wear naturally reduces the ability of the teeth to shear away, remove, the tissue the teeth are employed to remove. In some procedures, such as laminectomies, the tip is required to, over the course of the procedure, remove significant amount of tissue. Over time, the wear of the teeth results in appreciable loss in the ability of the tip to perform the intended tissue removal. This may require the surgeon to interrupt the procedure to substitute the tip with the worn teeth with a new tip the teeth of which are not worn. Having to so interrupt a procedure to replace a tip increases the time it takes to perform the procedure. Increasing the length of time it takes to perform a surgical procedure runs contrary to one of the accepted best techniques of modern surgical practice. A procedure should be performed as quickly as possible to minimize the time the patient is exposed to anesthesia. A second reason to perform a procedure as quickly as possibility is to minimize the time to which the patient's normally concealed internal tissue is exposed to the ambient environment and the infection-causing agents inherently in this environment.

In theory, it should be possible to coat the head and teeth of an ultrasonic tip with a layer of material such as diamond like carbon. This would increase the hardness of the teeth. By extension, this would reduce the rate at which the teeth wear in comparison to uncoated teeth. One disadvantage of providing a tip with type of coating is the presence of the coating would cause the resonant frequency of the tip to move away from the resonant frequency of the drivers internal to the handpiece to which the tip is attached. The resonant frequency is the frequency at which, when the drive signal is at given voltage or current, the application of the drive signal at that frequency induces vibrations in the tip that are at a relatively large amplitude in comparison to the application of the same voltage or current at a frequency that is off resonance. Ideally, a tip should have a resonant frequency that, as closely as possible, matches the resonant frequency of the drivers. As the resonant frequency of the tip moves away from the resonant frequency of the drivers, the ability of the tip transfer the mechanical energy of the drivers to the teeth is reduced. This reduces the efficiency of the removal of the tissue by the tip.

There is another reason why adding a coating to the head of an ultrasonic tip may not be the optimal means of increasing the hardness of the tip's teeth. The vibrating of the tip may result in the tip and coating vibrating at different frequencies. This can result the material forming the coating delaminating off of the tip. These delaminated bits of tip, owing to gravity, can fall into the open surgical site at which the procedure is being performed. Clearly, an undesired result of any surgical process is the introduction of unwanted material into the body of the patient.

SUMMARY

This description is related to the structure of a surgical ultrasonic cutting accessory with at least one cutting edge. More particularly the cutting accessory of this description is formed so that the surfaces of the accessory that meet to form the at least one cutting edge are case hardened. This case hardening reduces the wear of the surfaces forming the at least one cutting edge of the cutting accessory without adversely affecting the ultrasonic and acoustical properties of the accessory. One such cutting accessory of this description is a surgical ultrasonic tip with teeth that are case hardened. This case hardened layer reduces the wear of the teeth. This description is also directed to a method of manufacturing this type of ultrasonic cutting accessory.

A tip of this cutting accessory includes an elongated stem and a head that is located at the distal end of the stem. Teeth project outwardly from the stem. The teeth are shaped to scrape away, remove, the tissue to which the teeth, when vibrated are applied. A further feature of this description is that material that hardens the tip is diffused into the outer layer of the teeth. In some versions of the accessory the material is diffused into a distal portion of the neck of the tip and the tip head. Since the teeth are part of the tip head it is understood that the hardening material is diffused into the teeth. The hardening material may be diffused into only the head. The hardening material may be only diffused into the teeth. The resultant hardened layer is sometimes referred to as a case hardened layer.

The tip may be manufactured from a titanium alloy. The material that is diffused into the outer layer of the teeth may be nitrogen.

In one method of assembling a tip of the accessory, the tip is machined to form the head, including the teeth. The machined tip is placed in chamber in which a significant percentage of the ambient gas is a gaseous form of the hardening agent. Only the portion of the tip that is to be hardened is subjected to a targeted heating process. This heating is performed to cause the sections of the tip into which the hardening agent is to be diffused to rise to a temperature at which the gaseous state hardening agent will diffuse into the outer layer of the section of the tip to be hardened. In some of these versions of the method, a laser may be directed to the teeth. The photonic energy, (the light) of the laser beam heats the teeth to a temperature at which the hardening agent will diffuse into the outer layer of the teeth.

In an alternative version of the method, after the tip is machined, a mask is disposed over the sections of the tip that are not to be hardened. Once the tip is so masked, the tip is placed in a chamber in which a significant percentage of the ambient gas is a gaseous form of the hardening agent. The chamber is then heated so the tip rises to a temperature at which the hardening agent will diffuse into the outer layer of the tip. More particularly, as a result of this heating of the tip, the hardening agent diffuses into the unmasked portions of the tip. These unmasked sections of the tip are the sections of the tip into which it is intended the hardening agent be present.

In a third method of manufacture of this invention, the tip is formed by a laser cutting process. In this type of processes a focused beam of light, a laser beam, is applied to the workpiece from which the tip is to be formed. At a minimum, the laser beam is used to shape the teeth. Simultaneously with the application of the laser beam an assist gas is directed towards the workpiece. The assist gas is applied to the workpiece along a vector that is close to if not overlaps the vector along which the laser beam is applied. The assist gas blows the metal that is turned into the molten state by the laser beam away from the workpiece. A substantial fraction of the assist gas is a gaseous state form of the hardening agent.

Thus, in this example method of manufacture, the application of the assist gas to the workpiece performs two functions. The gas removes the cut molten state metal away from the workpiece to facilitate the shaping of the workpiece into the tip. During this process, the assist gas flows over the heated skin of the workpiece as the workpiece is shaped into the tip. Given that this section of the tip is heated, the fraction of the hardening agent in the assist gas stream will diffuse into the tip. Thus, the assist gas serves as the media that applies the hardening agent to the tip so as to foster the diffusion of the hardening agent into the tip.

BRIEF DESCRIPTION OF THE DRAWINGS

The invention is pointed out with particularity in the claims. The above and further features and benefits of this invention are understood from the following Detailed Description taken in conjunction with the following drawings in which:

DETAILED DESCRIPTION

Figure 1:
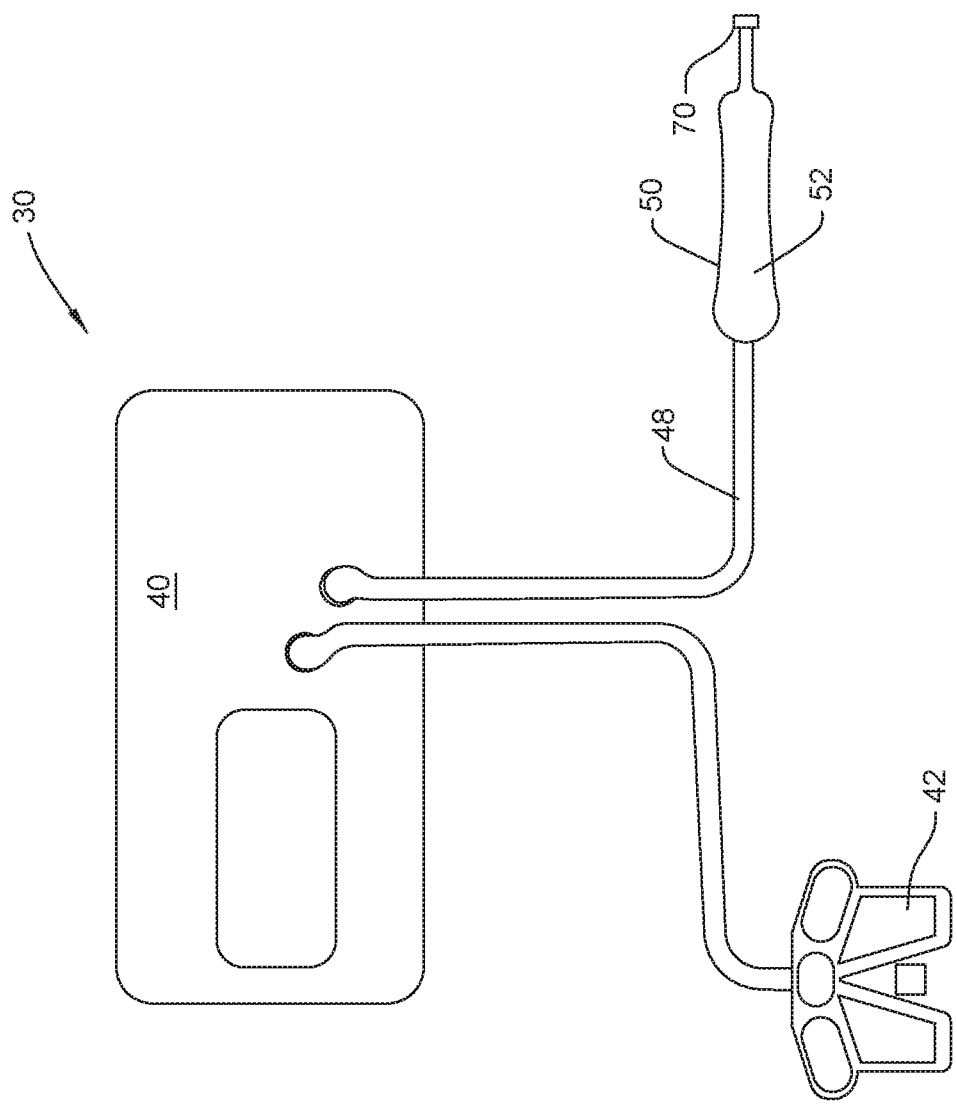
FIG. 1 depicts the basic components of an ultrasonic surgical tool system that includes the tip of this description.
Figure 2:
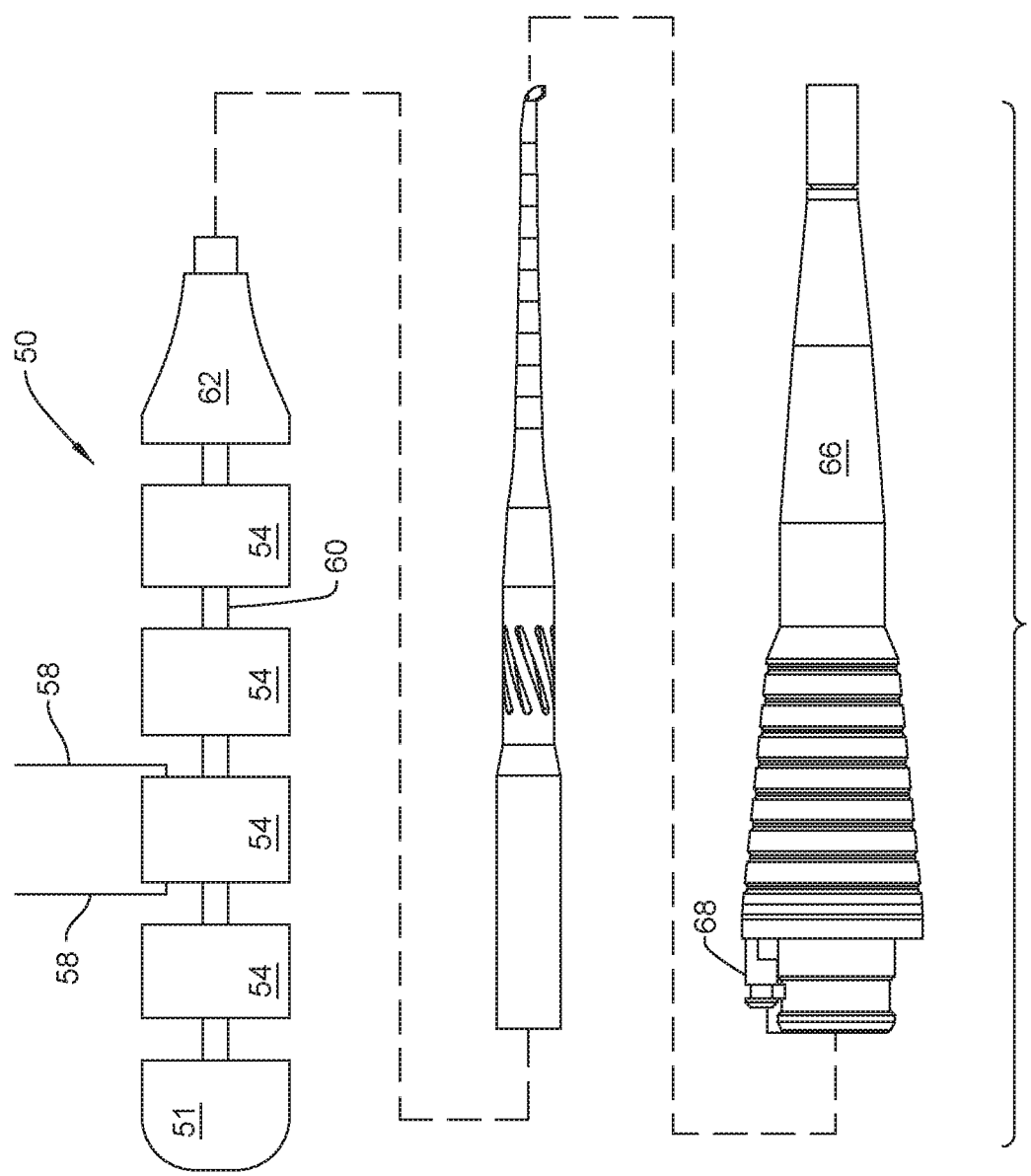
FIG. 2 is a diagrammatic depiction of the components of the handpiece, including the tip, of the system of FIG. 1.

FIGS. 1 and 2 depict a powered surgical tool system 30 that includes an ultrasonic tip 70 of this description. System 30 includes a handpiece 50, sometimes called an ultrasonic surgical tool or an ultrasonic aspirator or an ultrasonic handpiece. Handpiece 50 includes a body or shell 52 that forms the proximal end of the handpiece. ("Proximal" is understood to mean towards the practitioner holding the handpiece, away from the site to which the handpiece is applied. "Distal" is understood to mean away from the practitioner, towards the site to which the handpiece is applied.) The body 52 is the portion of the handpiece 50 that is actually held by the medical practitioner. Tip 70 extends distally forward of the handpiece 50.

One or more vibrating piezoelectric drivers 54 (four shown) are disposed inside shell 52. In FIG. 2 the handpiece shell 52 is not seen so the internal components of the handpiece 50 are exposed. Each driver 54 is formed from material that, when an AC voltage is applied to the driver, undergoes a momentary expansion or contraction. These expansions/contractions are on the longitudinal axis of a driver 54, the axis that extends between the proximally and distally directed faces of the driver. A pair of leads 58, only two leads seen in FIG. 2, extend away from each driver 54. The leads 58 are attached to the opposed proximally and distally directed faces of the drivers 54. Many, but not all handpieces 50, include piezoelectric drivers 54 that are disc shaped. These drivers 54 are arranged end to end in a stack. Leads 58 are the components of system 30 which the voltage, in the form of a drive signal, is applied to the drivers 54. In FIG. 2, drivers 54 are shown spaced apart from each other. This is for ease of illustrating the components. In practice, drivers 54 tightly abut.

The drivers 54 are understood to convert the electrical energy applied to the drivers to mechanical power. Accordingly, drivers 54 collectively function as the (mechanical) power generator of the system 30.

A post 60 extends longitudinally through drivers 54. The post 60 extends through the drivers 54 along the collinear longitudinal axes of the drivers. Not seen are through bores internal to the drivers 54 through which post 60 extends. Post 60 projects outwardly of both the most proximally located driver 54 and the most distally located driver 54.

A proximal end mass 51 is located adjacent the proximally directed face of the most proximally located driver 54.

The exposed proximal end section of the post 60 is fixedly attached to mass 51. If post 60 is threaded, then mass 51 may be a nut.

A horn 62 extends forward from the distally directed face of the most distally located driver 54. While not shown, an insulating disc may be between the distal driver 54 and horn 62. Horn 62 has a proximal end base with a diameter approximately equal to the diameter of the drivers 54. Extending distally forward from the drivers 54, the diameter of the horn 62 decreases. The exposed distal end section of post 60 is affixed to the horn 62. If the post 60 is threaded, the horn base may be formed with a threaded bore (not identified) for receiving the post. Handpiece 50 is constructed so that the stack of drivers 54 is compressed between proximal end mass 51 and horn 62.

A sleeve 66 is typically disposed over the proximal portions of the tip 70. Sleeve 66 typically extends from a location near where the tip 70 is attached to the handpiece 50 to a location approximately 0.5 cm proximal to the most distal head 86 of the tip 70. Collectively, the handpiece 50, sleeve 66 and tip 70 are constructed so that the sleeve defines a fluid flow conduit that extends between the outer surface of the tip and the surrounding inner surface of the sleeve. The sleeve 66 has a fitting 68 adjacent the proximal end of the sleeve that extends to this conduit. The conduit is open at the distal end of the sleeve 66. When the handpiece 50 is in use, irrigating solution is flowed from the sleeve fitting 68, down the sleeve and discharged adjacent the tip head 86. In some versions of the system, the fluid serves as a medium through which the mechanical vibrations of the tip head are transferred to the tissue. This irrigating solution also functions as a heat sink for the thermal energy developed by the tip head 86 as a consequence of the vibration of the head.

Handpiece post 60, horn 62 and tip 70 are often formed with conduits. Not seen are the conduits internal to the post 60 and horn 62. These conduits collectively define a fluid flow path from the tip head 86 to the proximal end of the handpiece 50. When handpiece 50 is in operation, suction is drawn through these conduits. The suction draws the irrigating fluid discharged through the sleeve 66 away from the site to which the tip is applied. Entrained in this irrigating fluid are debris generated as a result of the actuation of the tip 70. The suction also draws the tissue towards the tip head 86. The shortening of the distance between the tip head and the tissue improves the transmission of the mechanical vibrations from the tip head to the tissue that is to be subjected to removal.

A handpiece 50 of system 30 able to draw suction is sometimes referred to as an aspirator or an ultrasonic aspirator.

From FIG. 1 it can be seen that system 30 includes a control console 40. Internal to the console 40 are components that output an AC drive signal that is applied to the handpiece drivers 54. In some versions of the description this drive signal is between 10 kHz and 100 kHz. Often this drive signal is between 20 kHz and 50 kHz. The structure of the console 40 is not relevant to this particular description. Footswitch 42 represents the component actuated by the surgeon to both actuate the console and set the characteristics of the drive signal. Further understanding of the structure of the console can be obtained from patent publications WO 2015/021216 A1, WO 2016/183084 A1 and WO 2017/210076 A2, each of which is explicitly incorporated herein by reference.

Control console 40 sources drive signals over a cable 48 to which handpiece 50 is connected. It is common, but not required, to assemble cable 48 and handpiece 50 as a single unit.

Figure 3:
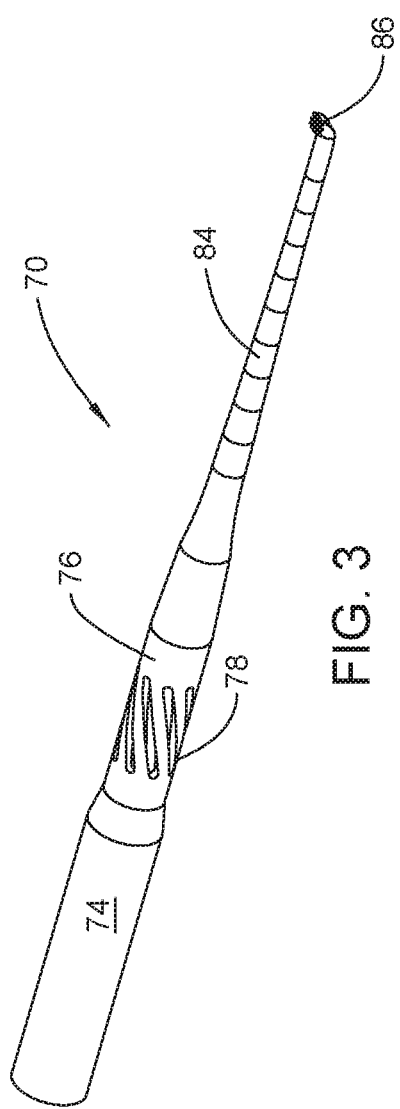
FIG. 3 is a perspective view of a tip of this description.
Figure 4:
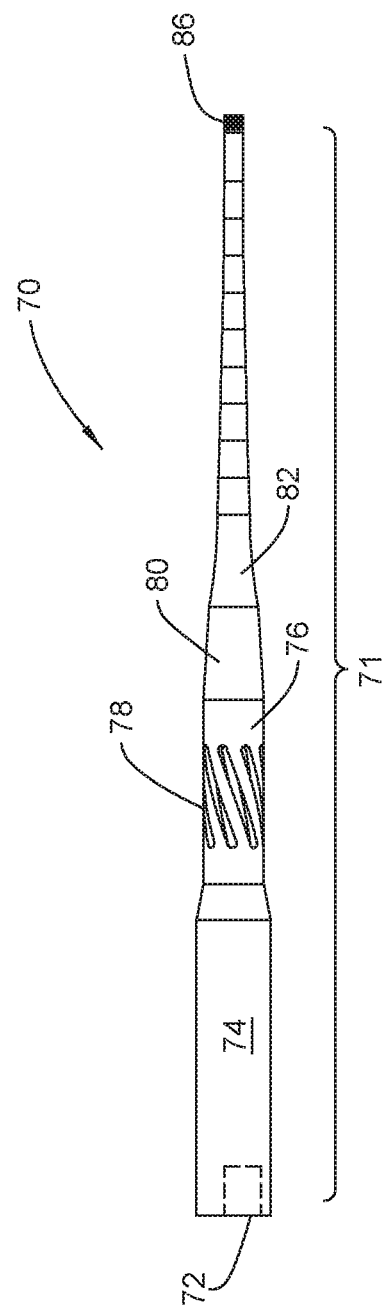
FIG. 4 is a top plan view of the tip.
Figure 5:
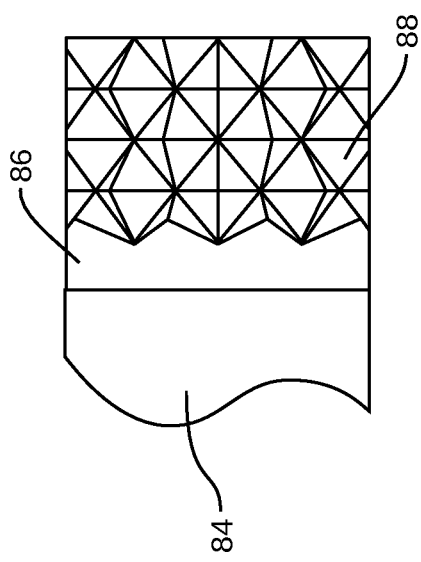
FIG. 5 is an enlarged top plan view of the head of the tip.

Tip 70 of this description, as seen in FIGS. 3 and 4, is a single piece unit. The tip 70 is formed out of titanium or an alloy of titanium. One titanium alloy from which the tip 70 can be formed in Ti-6Al-4V. Titanium Ti-6Al-4V is an alloy of titanium that by weight is approximately 6% aluminum, approximately 4% vanadium, the remainder substantially titanium. The tip 70 is formed to have a number of different sections. At the most proximal end tip 70 has a base 74. Base 74 is cylindrical in shape. The proximal end of the base 74, which is the proximal end of the tip 70, may be formed with features that facilitate the releasable coupling of the tip 70 to the horn 62. In FIG. 4 a closed end bore 72 is shown extending distally from the proximal end of the base partially through the base. Bore 72 represents that the base 74 is typically formed with features to tightly releasably mechanically couple the tip 70 to the horn 62. For example, the horn 62 may have a threaded boss. The inner surface of the tip that defines bore 72 may be formed with threading that engages the threading of the boss. The actual tip components that facilitate the releasable coupling of the tip 70 to the horn 62 are not part of the present description.

Extending forward from the base 74 tip 70 has a torso 76. The torso 76 is cylindrical in shape and has a diameter less than that of the base 74. Not identified is the tapered transition section between the base 74 and the torso 76. The illustrated torso 76 is formed with helical slots 78. Owing to the presence of slots 78, when the horn 62 vibrates the tip 70 longitudinally, that is proximally to distally along the longitudinal axis of the tip, the sections of the tip distal to the slots also engage in vibrations that are torsional. Torsional vibrations are understood to be vibrations around the longitudinal axis that extends between the opposed proximal and distal ends of the tip 70.

Forward of the torso 76, tip 70 has two transition sections 80 and 82. Transition section 80 is the section immediately distal to the torso 76. Transition section 82 extends forward from transition section 80. Both transition sections are tapered. The diameter of each section 80 and 82 decreases as the section extends distally forward. The taper of section 82 is steeper than the taper of section 80. Tip 70 has a stem 84 that extends forward from transition section 82. Stem 84 has a shallow taper. The taper of stem 84 is less than the taper of transition section 82. Tip 70 is formed so the stem subtends a length that is approximately 25% to 50% of the total length of the tip.

The head 86, located at the distal end of stem 84, is the most distal section of the tip 70. One side of the head may project laterally outwardly from the adjacent distal section of the stem 84. This section of the head 86 is formed with teeth 88. Teeth 88 project laterally outwardly from the head 86. The teeth 88 thus project outwardly from the longitudinal axis of the tip 70. Each tooth may be generally in the form of a four-sided pyramid. The edges where two sides of tooth meet form a cutting edge of the tooth. The point from which the sides of a tooth extend outwardly is the cutting point of a tooth.

Figure 6:
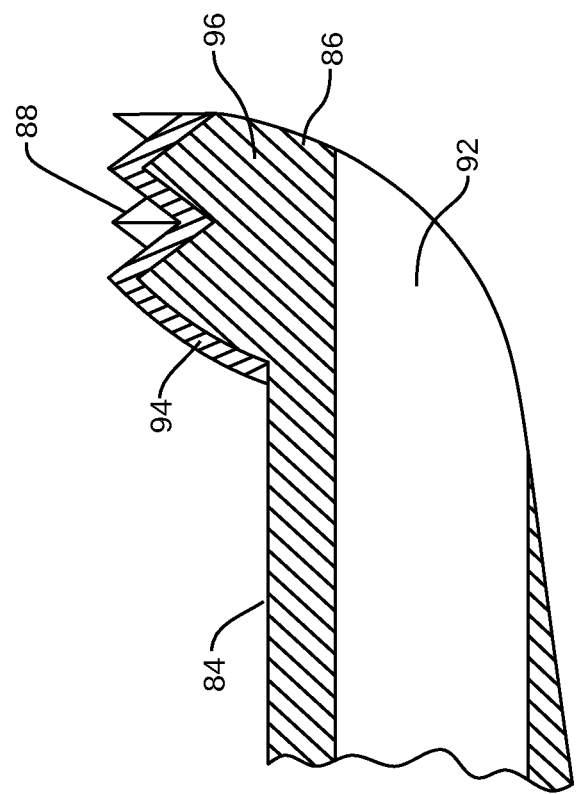
FIG. 6 is a cross sectional view taken along line 6-6 in FIG. 5 of the head of the tip and the adjacent distal portion of the stem of the tip.

In FIG. 6 a bore 92 can be seen extending proximally from the distally directed face of head 86. Bore 92 extends distally through head 86 and stem 84. While not seen it should be understood that bore 92 opens up into the closed end of bore 72. Bore 92 is the conduit through which suction is drawn through the tip 70.

While tip 70 is formed from a single piece of metal, a hardening agent is embedded in at least the outer portion of the teeth 88. In FIG. 6, core 96 represents the portion of the head 86, including the teeth 88, in which the hardening agent is not present. Layer 94 the outer layer of teeth in which the hardening agent is present. Layer 94 is sometimes called the case hardened layer. One such hardening agent that can be embedded in the teeth is nitrogen. The case hardened layer 94 may extend at least 1 micron into the tip from the outer surface of the teeth. Often the case hardened layer 94 extends at least 3 microns into the tip from the outer surface of the teeth. In most versions, the case hardened layer may not extend more than 50 microns into the tip from the outer surface of the teeth.

The ultrasonic handpiece 50 is used by positioning head 86 integral with the tip 70 in close proximity to the tissue to removed. The handpiece 50 is actuated by sourcing a drive signal from the console 40 to the drivers 54. The resultant cyclic expansions/contractions of the driver 54 results in the vibration of the tip and more particularly, the tip head 86 and teeth 88. The tip head is positioned so the teeth 88 bear against the tissue to be cut. The back and forth movement of the teeth 88 against the tissue results in the shearing away of, the removal of, the tissue.

The presence of hardened layer 94 of the teeth 88 means that the teeth, when they shear against the tissue to be removed are less prone to wear than the teeth of an identical tip that does not include the hardened layer. Consequently, in comparison to a conventional tip, a tip without the hardened layer being present, there is less likelihood that, during a procedure, tip 70 will wear to the level at which there will be an appreciable decrease in the ability of the tip 70 to remove tissue. This results in a like reduction in the likelihood that, during a procedure, teeth 88 of tip 70 will become so worn that, to timely perform the procedure, it will be necessary to interrupt the cutting process to provide a new tip with sharp teeth.

A further feature of tip 70 is that the case hardened layer does not extend over the whole of the tip. To understand the limit of the extent to which a tip is provided with a hardened layer it should be understood that a tip has a fundamental vibrational mode. Many tips are designed to vibrate longitudinally. This means the tip is vibrated the head oscillates along a proximal to distal path that extends along a line coincident with the proximal to distal longitudinal axis through the tip. Other tips are designed to engage in torsional vibrations. When a tip vibrates torsionally, the head of the tip rotates around an axis close to if not centered on the longitudinal axis through the tip. Still other tips are designed to undergo flexural vibration. When a tip engages in flexural vibrations, the stem 84 bends relative to the linear extension of the longitudinal axis through the base 74 of the tip 70. This means that when the tip head 86 moves back and forth, to the left and the right, of the linear extension of the longitudinal axis through the base 74 of the tip 70. Some tips are designed to, when excited into vibrational movement, engage in vibrations that are combination of two or more or all three of the different types of vibrations: longitudinal; torsional and flexural.

Regardless of the type of vibrations the tip 70 is designed to undergo, there is a fundamental vibration mode associated with the tip. This mode is characterized by a resonant frequency. Each tip also has a characteristic wavelength. The length of this wavelength is the quotient calculated by dividing the speed of sound by the characteristic resonant frequency of the fundamental vibration mode. This characteristic resonant frequency is sometime referred to as the natural frequency of the vibration mode of interest.

For the purposes of this description, the "characteristic resonant frequency" is understood to be the resonant frequency of the tip, when vibrated, at the ambient environment and the tip is not subjected to mechanical loading. This characteristic resonant frequency is typically a function of the following characteristics of the tip: material; shape; and dimensions. Based on these variables, mathematical processes such as finite element analysis can be used to determine this frequency. Post manufacture, it is possible to determine the characteristic resonant frequency of a tip by vibrating the tip at a number of frequencies centered on what is to believe the characteristic resonant frequency of the tip. The frequency at which the vibrations are of greatest magnitude may be considered the characteristic resonant frequency of the tip. The finite element analysis and the empirical of vibrating the teeth may be combined to determine the characteristic resonant frequency of the tip 70.

It is believed that the case hardened layer 94 should be formed over the all the teeth 88 and extend proximally a distance from the proximal most tooth 88 that is a maximum of one-eighth of the length of the characteristic wavelength. Thus, the case hardened layer 94, may extend over the whole of the head 86 and an adjacent distal section of the tip stem 84. The case hardened layer 94 may alternatively only extend over the head 86 of the tip. Yet alternatively, only the teeth 88 may include the case hardened layer 94.

It should be understood that the distal end head 86 of a tip 70 is, in terms the vibratory movement of the tip, the anti-node. (For the purposes of defining a point location for the antinode, the proximal most tooth 88 is considered the point on the head 86 where this anti-node exists.) This means that while the head 86 itself engages in vibratory movement relative to a reference point in space, the atomic material forming the head and teeth 88 does not itself engage in inter atomic vibratory movement (vibratory movement between adjacent atoms). The movement of the of the tip head 86 and teeth 88 is due to the inter atomic vibratory movement that occurs proximal to the head. This movement is at a maximum at the vibratory node and decreases distally from this node. This node is located a distance of one-quarter of the characteristic wavelength proximal to the anti-node. Thus it should be appreciated that the wave of the characteristic wavelength is a wave of the extent to which individual sections of the tip extending distally to proximally along the tip, engage in different magnitudes of inter-atomic vibratory motion.

The hardened layer 94 and the underlying layer of the tip naturally have different degrees of stiffness. If both layers simultaneously expand/contract, twist and/or bend, owing to these layers having different stiffness, the inherent tendency would be for the outer hardened layer to, over time, separate from the underlying layer.

If this separation occurs over an opening into the patient, there is possibility that the cracked off portions of the hardened layer could fall against the internal tissue of the patient. To avoid infection and irritation of the tissue, this is a result of the tip that practitioners naturally want to avoid.

However as described above, the node of maximum inter atomic vibration is located a distance proximal to the teeth that is a distance of one-quarter the characteristic wavelength of the tip 70 from a location proximal to the head 86. The hardened layer 94 typically only extends a distance of one-eighth the characteristic wavelength proximal to the head 86. This means that the hardened layer 94 is spaced a distance of at least one-eighth the length of the characteristic wavelength from where the maximum inter atomic vibrations are occurring.

Hardened layer 94 is thus spaced distally away from where molecules forming tip 70 are subjected to their greatest inter molecular, vibration-induced stress. The expansion/contraction, twisting or bending of adjacent molecules that occurs at and near the vibratory node only nominally, if at all, occurs where the hardened layer 94 is embedded into the tip. Consequently, the vibratory movement necessary to induce the desired vibrations of the tip head 86 does not result in stress between the atomic material forming the hardening agent and the atomic material into which the hardening agent is embedded. Tip 70 is therefore designed so that the likelihood that the material forming the case hardened layer 94 will be subjected to vibratory stress is substantially eliminated. The substantial elimination of this stress results in a like substantial elimination that this stress can cause the material forming the case hardened layer 94 to separate from the rest of the tip 70.

Figure 7:
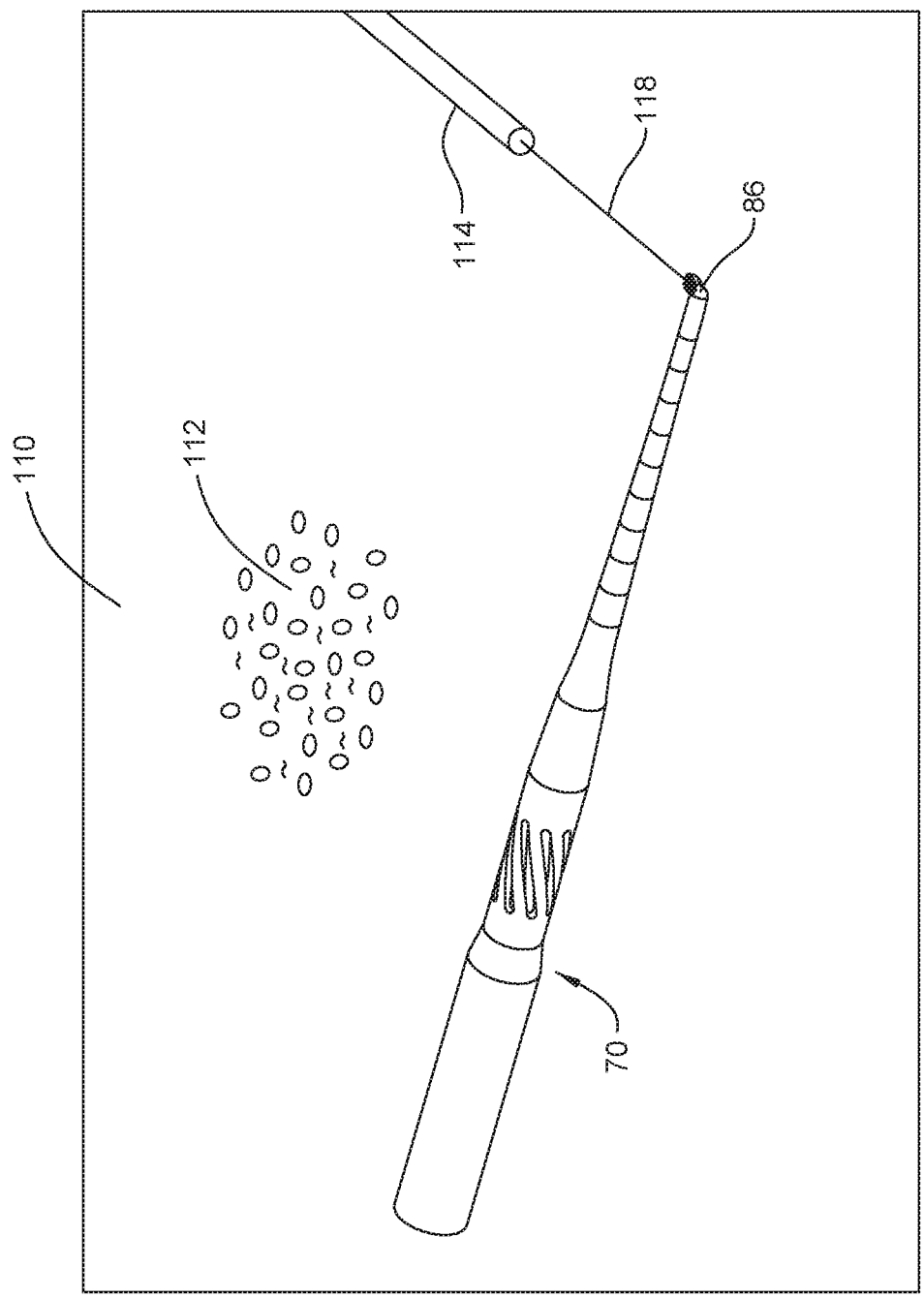
FIG. 7 depicts a first method of fabricating a tip of this description.

One means to manufacture a tip 70 is now described by reference to FIG. 7. In this method of manufacture, the tip 70 is initially completely shaped. This means, by grinding, machining or coining or three-dimensional printing the whole of the tip 70, including base 74, intermediate sections 76 and 80, slots 78, stem 84, head 86 and teeth 88, are formed. For the purposes of this operating, base 74, intermediate sections 76 and 80 and stem 84 are collectively considered the shaft 71 of the tip. Once the tip 70 is fully shaped, the tip is placed in a chamber 110. The environment in the chamber is set so the gas in the chamber includes an appreciable fraction of the gaseous state hardening agent. Dots 112 represent the gaseous state hardening agent. If Nitrogen is employed as the hardening agent the chamber 110 is substantially filled with $N_2$ gas and the purity of the gas is typically at least 97% if not 99% or greater. The pressure within the chamber is typically a minimum of 1 Atmosphere and may be as high as 4 Atmospheres.

Once the environment in chamber 110 is established, a beam of light 118 from a laser 114, is directed to the portions of the tip 70 into which the hardening agent is to embed. The photonic energy of the light beam 118 heats the portions of the tip against which the light beam is applied. More specifically, these portions of the tip are heated to a temperature at which the gaseous state hardening agent will diffuse across the outer surface of the heated section of the tip and into the layer of the tip below this surface. When the tip is formed from Ti—Al-4V, the surface of the tip is often heated to a temperature of between 700 and 1700° C. More specifically, the hardening agent diffuses into the lattice of the metal forming the tip. This heating is often between 30 seconds and 3 minutes for each portion of the tip into which the hardening agent is to be embedded. When the heating is of this short duration the heating does not result in the liquefaction of the metal forming the tip to the extent to which the shape of the tip will be deformed. This heating does, however, cause the vibrational range of the atoms forming the teeth to increase. This increase in range of vibrational movement of the atoms causes the atoms to move a sufficient distance so the hardening agent diffuses through the surface of the tip. The diffusion of the hardening agent into the teeth result in the formation of the case hardened layer 94.

It should be understood that by varying the length of time the section of the tip is heated, the depth to which the nitrogen embeds in the tip to form the case hardened layer 94 can be controlled. The longer the section of the tip is heated, the deeper the hardening agent will embed into the tip.

Figure 8:
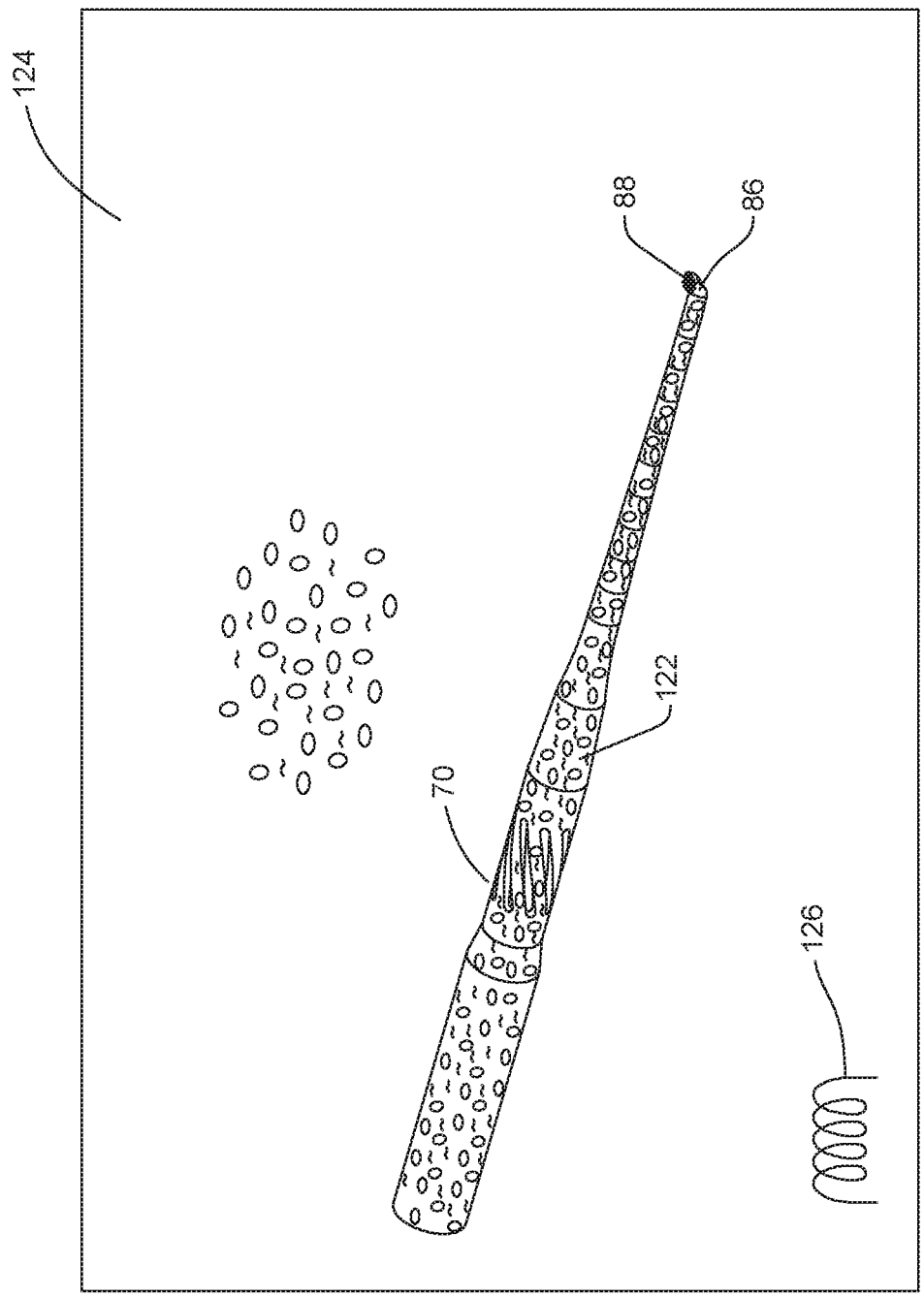
FIG. 8 depicts a second method of fabricating a tip of this description.

A second method of manufacture may be understood by reference to FIG. 8. In this method of manufacture, as in the first method of manufacture, the tip, including the sections of the tip to which the hardened layer is to be added, is fully shaped. A mask 122 is disposed over the sections of the tip to which a hardened layer is not be formed. In FIG. 8, the mask 122, depicted as stippling, is disposed over the sections of the tip into which the hardening agent is not be diffused. If nitrogen is employed as the hardening agent, the mask may be masking paint.

Once mask 122 is disposed over the tip 70, the tip is placed in a chamber 124. The environment of chamber 124 is set so as to be rich in a gaseous state form of the hardening agent. In FIG. 8 dots 112 represent the gaseous form of the hardening agent. The chamber 124 is then heated to a temperature at which the hardening agent will diffuse into the unmasked portions of the tip. Coil 126 internal to the chamber 124 represents the components that heat the inside of the chamber.

As a result of the heating of the tip 70, the atoms forming the tip expand apart a sufficient distance apart from each other so that the hardening agent is able to diffuse across the outer surface of the tip. More particularly, the hardening agent diffuses across the unmasked sections of the tip. The hardening agent that diffuses into the tip hardening agent thus forms the case hardened layer 94 of the tip on the sections of the tip at which such layer is wanted.

Figure 9:
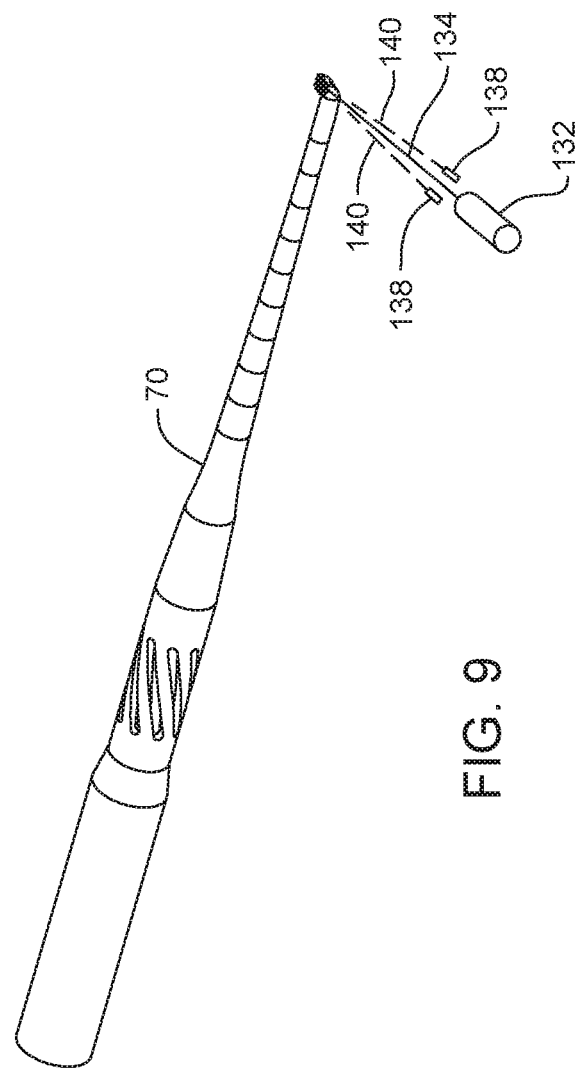
FIG. 9 depicts a third method of fabricating a tip of this description.

FIG. 9, discloses a third method of manufacturing a tip 70. The tip is initially first only partially shaped. More particularly, the section of the tip into which the hardened layer is not to be embedded are shaped.

Once the tip is partially shaped, a laser 132 is used to shape the portions of the tip into which the hardened layer is to be formed. In this process, a beam of light (photonic energy), represented by solid line 134, is directed to the sections of the tip to be shaped. The energy of the beam is absorbed by and heats the partially assembled tip. The heating of the tip results in the surface of the tip reaching a molten state.

Simultaneously with the light being applied to the tip 70 a jet of assist gas is applied to the tip. The assist gas is applied from a nozzle 138 so as to flow over the section of the tip being heated to a molten state. In FIG. 9 two nozzles 138 are shown. Dashed lines 140 represent the flow, i.e., stream or streams of assist gas from the nozzles 138. The assist gas may be composed at least in part of a gaseous form of the hardening agent.

The jet of assist gas, upon striking the tip 70, performs two functions. First the jet of assist gas blows the molten state material away from the rest of the tip. The removal of this material within microseconds of being formed facilitates the shaping of the tip. The second function the assist gas performs is due to the fact that the assist gas is at least partially composed of the gaseous state form of the hardening agent. Accordingly, given that the remaining portion of the tip is in a heated state, a fraction of the hardening agent forming the jet of assist gas will diffuse across the surface of the tip.

Thus the application of the jet of assist gas results during the application of a laser beam to shape the tip results in the simultaneous shaping of the tip and the diffusion of the hardening agent into the tip.

Alternative versions of this description may be possible. For example, the materials from which both the tip and hardening agent are formed may be different from what has been described. In alternative versions of the description, the tip may be formed material other than Titanium based materials. Generally the tip is formed metal. Metals from which the tip may be formed include iron-based alloys and aluminum based alloys. In alternative versions of the description, carbon or boron may be employed as the hardening agent.

Methods other than described methods may be employed to form the case hardened layer of the tip. For example, an induction coil may be used to heat the tip during the process of embedding the hardening agent in the tip. In FIG. 9, the paths along which the laser beam 134 and streams 140 of assist gas are applied to the tip are shown as being angled relative to each other. These paths may be coaxial. The laser beam and assist gas may be applied in the same direction to the tip. Alternatively, the laser beam and the assist gas may be applied from oppose locations relative to the tip.

Further the described method may be used to form hardened layers of surgical cutting accessories other than the teeth of ultrasonic tips. Other surgical cutting accessories that can be provided with hardened layers according to the described method include saw blades, burs, drills and rasps. The method may be used to form case hardened layer on the features of other ultrasonic cutting accessories that have cutting edges. For example, this method may be employed to form case hardened layers on the adjacent surfaces of an ultrasonic scalpel that meet to form the cutting edge of the scalpel.

It should thus be appreciated that other ultrasonic cutting accessories may have different shapes. For example, not all ultrasonic tips may have shafts that have linear longitudinal axes. A tip may have a shaft with proximal and distal sections that are angled relative to each other. The proximal section extends outwardly from the handpiece 50 along a first longitudinal axis. The distal end of the shaft, the end from which teeth extend is centered on a second longitudinal axis. This second longitudinal axis is angled relative to the first longitudinal axis. Between the proximal and distal sections, the shaft has an intermediate section. The intermediate section connects the proximal and distal sections and is curved or bent. Thus, the intermediate section has a curved or bent longitudinal axis.

Not all ultrasonic tips as described herein may have features that convert a fraction of the longitudinal vibrations into torsional vibrations. Some described ultrasonic tips may have features that facilitate the flexural vibration of the tip head. This flexural vibration is understood to be a bending of the shaft so that the tip head moves in arc towards and away from a line that would be an extension of the longitudinal axis of the base of the tip.

Similarly, it should be appreciated that not all cutting accessories fabricated according to this description may be single piece units. For example, an ultrasonic tip that is relatively long in length, 15 cm or more in length, may be a two piece assembly. The base 74 and first intermediate section 76 may form a first piece. The second intermediate section 80, stem 84 and form a second piece. These two pieces are after being individually manufactured are threaded together. Accordingly, only the distal end piece, the piece with the surfaces forming the cutting edges that are to be case hardened, are subjected to the case hardening process.

Likewise, while not typical, some tips may be formed with a single tooth.

Likewise, it should be understood that when manufacturing tips as described herein, it will typically not be necessary to, for each tip, determine the characteristic resonant frequency in order to then determine the characteristic wavelength. Typically, once a tip is designed, mathematical processes and/or the empirical analysis (the frequency sweep process) are used to determine the characteristic resonant frequency for the tip. This characteristic resonant frequency is assigned to as the characteristic resonant frequency for tips having the same shape and dimensions and formed from the same material as this tip. In practice, between any two supposedly identical tips, owing to manufacturing tolerances, there may be minor variations in the characteristic resonant frequencies of the tips and, by extension, their characteristic wavelengths. These variations do not typically adversely affect the processes used to determine the extent to which the hardening agent should be embedded along the length of the tip.

Variations in the process of manufacturing a surgical instrument according this description are also possible. For example, while it is preferably that the tip be completely shaped before the hardening agent is diffused into the distal end of the tip, this is not always required. There may be manufacturing reasons to first only form the head 86, at least one tooth 88 and a small adjacent portion of the shaft. Then, the hardening agent is diffused into the portion of the tip in which the hardening layer is be formed. After these steps are completed, the rest of the stem 84 of the tip is formed.

Also, while targeting heating of the tip or the workpiece from which the tip is formed is typically performed with a laser, it may not be needed to use a laser in method of targeted heating performed to fabricate a tip according to this description. For example, an induction coil may be used to perform the targeted heating of a portion of the tip according to this description. Thus, induction heating may be used for a short period of time to simultaneously heat plural surfaces of one or more teeth to facilitate the diffusion of the hardening agent into these plural surfaces.

It should be likewise understood that the method described herein may be employed to case hardened layers of articles other than the cutting accessories of power surgical tools. Thus, the method described herein may be used to harden the teeth of a saw blade used to cut objects such as wood, plastic metal or concrete.

Accordingly, it is an object of the appended claims to cover all such variations and modifications that come within the true spirit and scope of this description.

What is claimed is:

1. A method of forming a tip for use with an ultrasonic handpiece that includes at least one driver that, when actuated, induces vibrations in the tip attached to the handpiece, said method including the steps of:
    at least partially shaping a tip to form at least a portion of a shaft of the tip, a head at a distal end of the shaft and at least one tooth that projects outwardly from the head;
    determining a characteristic wavelength of the tip; and
    diffusing a hardening agent into a distal portion of the tip wherein the hardening agent is at least diffused into the at least one tooth so that at least the at least one tooth has a case hardened outer layer and wherein, in said step of diffusing a hardening agent into the tip, the hardening agent is diffused along a length of the tip that, extends proximally from the at least one tooth and is a maximum distance of one-eighth of the length of the characteristic wavelength of the tip.

2. The method of forming a tip of claim 1, wherein:
    in said step of at least partially shaping the tip, the tip is shaped to have a plurality of teeth; and in said step of diffusing a hardening agent into the distal portion of the tip, the hardening agent is at least diffused into the plurality of teeth.

3. The method of forming a tip of claim 1, wherein said step of determining the characteristic wavelength of the tip is performed by:
  determining a characteristic resonant frequency of the tip; and
  determining the characteristic wavelength of the tip as a function of the characteristic resonant frequency of the tip.

4. The method of forming a tip of claim 3, wherein:
  said step of determining a characteristic resonant frequency of the tip is performed by determining the characteristic resonant frequency for a tip having features of the tip to be subjected to said step of diffusing the hardening agent into the distal portion of the tip; and
  said step of determining the characteristic wavelength of the tip is based on the characteristic resonant frequency for the tip having the features of the tip to be subjected to said step of diffusing the hardening agent into the distal portion of the tip.

5. The method of forming a tip of claim 3, wherein said step of determining the characteristic resonant frequency of the tip is at least partially performed by performing finite element analysis of the tip.

6. The method of forming a tip of claim 3, wherein said step of determining the characteristic resonant frequency of the tip is at least partially performed by vibrating the tip at a number of different frequencies to determine the characteristic resonant frequency of the tip.

7. The method of forming a tip of claim 1, wherein said step of diffusing a hardening agent into the distal portion of the tip is performed by:
  after said step of at least partially shaping the tip, placing the tip in a chamber;
  setting an environment of the chamber so that, within the chamber, there is a gaseous state form of the hardening agent; and
  selectively heating an outer surface of the distal portion of the tip into which the hardening agent is to be diffused to a temperature at which the hardening agent will diffuse into the tip.

8. The method of forming a tip of claim 1, wherein said step of diffusing a hardening agent into the distal portion of the tip is performed by:
  after said step of at least partially shaping the tip, forming a mask over portions of the tip into which the hardening agent is not to be diffused;
  placing the tip in a chamber;
  setting an environment of the chamber so that, within the chamber, there is a gaseous state form of the hardening agent; and
  heating the inside of the chamber so a temperature of an outer surface of the tip rises to a level at which the hardening agent will diffuse into portions of the tip that are not covered by the mask.

9. The method of forming a tip of claim 1, wherein said step of at least partially shaping the tip to form the at least one tooth of said tip is performed by:
  directing targeted energy to the tip to heat a surface of the tip where the at least one tooth is to be formed to a molten state; and
  simultaneously with said step of directing targeted energy to the surface of the tip, directing an assist gas to a section of the tip being heated to the molten state, the assist gas including a gaseous state form of the hardening agent so that the assist gas blows molten state material away from the tip and so that a fraction of the gaseous state form of the hardening agent diffuses into a portion of the tip that remains after the molten state material is blown away so that said steps of at least partially shaping the tip to form the at least one tooth of the tip and diffusing the hardening agent into the at least one tooth are performed simultaneously.

10. The method of forming a tip of claim 1, wherein in said step of diffusing a hardening agent into the distal portion of the tip, the hardening agent is only diffused into the at least one tooth so that only the at least one tooth is formed with a case hardened outer layer.

11. The method of forming a tip of claim 1, further including the step of forming the tip so that the tip is formed with a bore through which a suction can be drawn.

12. The method of forming a tip of claim 1, further including the step of forming the tip with a feature that causes the at least one tooth to, when the tip is vibrated by the at least one driver, engage in plural different vibrational movements.

13. The method of forming a tip of claim 1, wherein said tip is shaped out of a single piece unit.

14. The method of forming a tip of claim 1, further including the step of shaping the tip so the shaft of the tip is linear in shape.

15. The method of forming a tip of claim 1, wherein in said step of at least partially shaping the tip, the tip is shaped out of: titanium; an alloy of titanium; aluminum; an alloy of aluminum; iron; or an alloy of iron.

16. The method of forming a tip of claim 1, wherein in said step of diffusing the hardening agent into the distal portion of the tip, a component of the hardening agent is selected from the group consisting of: boron; carbon; and nitrogen.

17. A tip for use with an ultrasonic handpiece, said tip manufactured according to the method of claim 1 and including:
  a shaft having opposed proximal and distal ends;
  a feature at a proximal end of the shaft for releasably coupling the shaft to an ultrasonic handpiece so said tip will, upon actuation of said handpiece, be vibrated by said handpiece; and
  a head that extends from the distal end of said shaft, said head formed to have at least one tooth,
  characterized in that:
  said at least one tooth has a case hardened outer layer.

18. The tip of claim 17, wherein said at least one tooth comprises a plurality of teeth extending from said head.

19. The tip of claim 17, wherein said shaft includes a bore through which a suction can be drawn.

20. The tip of claim 17, wherein said shaft has a feature that causes the at least one tooth to, when the tip is vibrated, engage in plural different vibrational movements.

21. The tip of claim 17, wherein said tip is shaped out of a single piece unit.

22. The tip of claim 17, wherein said shaft is linear in shape.

23. The tip of claim 17, wherein said shaft, said head and said at least one tooth are formed from: titanium; an alloy of titanium; aluminum; an alloy of aluminum; iron; or an alloy of iron.

* * * * *